(12) United States Patent
Dashevsky et al.

(10) Patent No.: US 10,598,003 B2
(45) Date of Patent: Mar. 24, 2020

(54) RESERVOIR MONITORING USING GALVANICALLY EXCITED TRANSIENT ELECTROMAGNETIC FIELDS

(71) Applicant: BAKER HUGHES INCORPORATED, Houston, TX (US)

(72) Inventors: Yuliy Aleksandrovich Dashevsky, Novosibirsk (RU); Alexandr Igorevich Makarov, Novosibirsk (RU); Elizaveta Vladimirovna Onegova, Novosibirsk (RU)

(73) Assignee: Baker Hughes, a GE company, LLC, Houston, TX (US)

( * ) Notice: Subject to any disclaimer, the term of this patent is extended or adjusted under 35 U.S.C. 154(b) by 109 days.

(21) Appl. No.: 15/123,887

(22) PCT Filed: Oct. 22, 2015

(86) PCT No.: PCT/RU2015/000699
§ 371 (c)(1),
(2) Date: Sep. 6, 2016

(87) PCT Pub. No.: WO2017/069650
PCT Pub. Date: Apr. 27, 2017

(65) Prior Publication Data
US 2017/0284190 A1    Oct. 5, 2017

(51) Int. Cl.
*G01V 3/18* (2006.01)
*E21B 47/10* (2012.01)
(Continued)

(52) U.S. Cl.
CPC ......... *E21B 47/102* (2013.01); *E21B 49/005* (2013.01); *E21B 49/08* (2013.01);
(Continued)

(58) Field of Classification Search
CPC ... E21B 49/005; E21B 49/08; G01N 33/2823; G01N 27/223; G01N 29/024; G01N 33/241; G01V 3/00; G01V 9/00
(Continued)

(56) References Cited

U.S. PATENT DOCUMENTS 7,340,348 B2 * 3/2008 Strack .................... G01V 3/083
                                                                702/14
9,551,806 B2 * 1/2017 Le ............................ E21B 49/00
(Continued)

OTHER PUBLICATIONS

Dutta, Sushant et al., "Modeling Tools for Drilling, Reservoir Navigation, and Formation Evaluation," Systemics, Cybernetics and Informatics, vol. 10, No. 3, pp. 81-87 (2012).
(Continued)

*Primary Examiner* — Raul J Rios Russo
(74) *Attorney, Agent, or Firm* — Mossman, Jumar & Tyler, P.C.

(57) ABSTRACT

Methods, systems, and devices for characterizing an anomalous fluid body in an earth formation using measurements in a borehole intersecting the formation. Methods include galvanically exciting a transient electric field in the earth formation which interacts with an anomalous fluid body in the earth formation remote from the borehole; galvanically receiving a corresponding transient electromagnetic (TEM) signal; and using at least one processor to estimate a value of a parameter of the anomalous fluid body using the corresponding transient signal.

12 Claims, 8 Drawing Sheets

(51) Int. Cl.
    *G01V 3/30*    (2006.01)
    *E21B 49/00*   (2006.01)
    *E21B 49/08*   (2006.01)
    *G01N 33/28*   (2006.01)
    *G01V 3/00*    (2006.01)
    *G01N 27/22*   (2006.01)
    *G01V 3/26*    (2006.01)
    *G01N 29/024*  (2006.01)
    *G01N 33/24*   (2006.01)
    *G01V 9/00*    (2006.01)

(52) U.S. Cl.
    CPC ....... *G01N 27/223* (2013.01); *G01N 33/2823* (2013.01); *G01V 3/00* (2013.01); *G01V 3/26* (2013.01); *G01V 3/30* (2013.01); *G01N 29/024* (2013.01); *G01N 33/241* (2013.01); *G01V 9/00* (2013.01)

(58) Field of Classification Search
    USPC .......................................... 324/323–377, 438
    See application file for complete search history.

(56) References Cited

U.S. PATENT DOCUMENTS

| | | | | |
|---|---|---|---|---|
| 9,903,977 | B2* | 2/2018 | DiFoggio | G01V 3/20 |
| 2008/0082269 | A1* | 4/2008 | Stoyer | G01V 3/12 |
| | | | | 702/6 |
| 2008/0136420 | A1* | 6/2008 | Velikhov | G01V 3/12 |
| | | | | 324/335 |
| 2010/0271030 | A1* | 10/2010 | Reiderman | G01V 3/28 |
| | | | | 324/338 |
| 2011/0315378 | A1 | 12/2011 | Homan | |
| 2013/0338923 | A1* | 12/2013 | Zhdanov | G01V 3/08 |
| | | | | 702/6 |
| 2015/0160367 | A1* | 6/2015 | Le | E21B 49/00 |
| | | | | 324/339 |
| 2015/0241592 | A1* | 8/2015 | Itskovich | G01V 3/28 |
| | | | | 324/341 |
| 2015/0285068 | A1* | 10/2015 | Morris | G01V 3/28 |
| | | | | 324/333 |
| 2016/0041291 | A1* | 2/2016 | Zhdanov | G01V 3/08 |
| | | | | 324/335 |
| 2016/0178787 | A1* | 6/2016 | Le | G01V 3/28 |
| | | | | 702/7 |

OTHER PUBLICATIONS

Colombo, Daniele, et al., "Quantifying Surface-to-Reservoir Electromagnetics for Waterflood Monitoring in a Saudi Arabian Carbonate Reservoir," Geophysics, vol. 78, No. 6, pp. E281-E297 (2013).

Int'l Search Report & Written Opinion in PCT/RU2015/000699, dated Dec. 5, 2016.

* cited by examiner

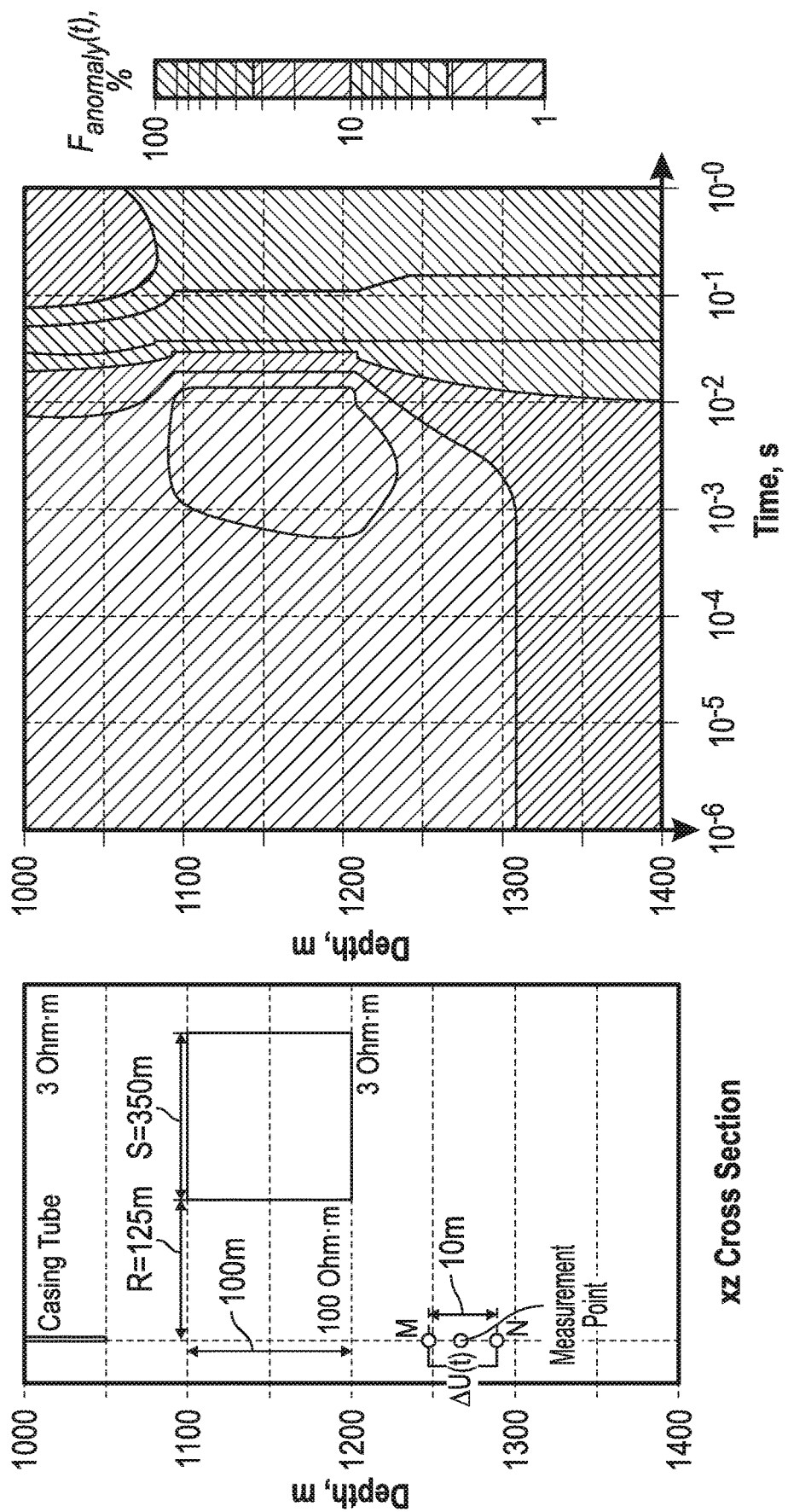

RESERVOIR MONITORING USING GALVANICALLY EXCITED TRANSIENT ELECTROMAGNETIC FIELDS

BACKGROUND

1. Field of the Disclosure

In one aspect, this disclosure generally relates to methods and apparatuses for characterizing a parameter of interest of an earth formation using electrical measurements. In another aspect this disclosure generally relates to methods and apparatuses for monitoring and management of fluids in an earth formation, such as a hydrocarbon reservoir. More particularly, a water flood process may be evaluated using time-lapse measurements.

2. Background of the Art

In many fields of endeavor, it may be useful to characterize a parameter relating to an earth formation, such as parameters relating to one or more fluids of the earth formation. For example, in exploration, development, and monitoring related to hydrocarbon production, it is important to make accurate measurements of geologic formations. The geologic formations below the surface of the earth may contain reservoirs of oil and gas or underground bodies of water. The geologic formations may include formation layers and various structures. In a quest for oil and gas, it is important to know about the location and composition of the formation layers and the various structures. In particular, it is important to know about the geologic formations with a high degree of accuracy so that resources are not wasted, particularly the behavior of subterranean fluids. In some applications it may also be useful to monitor fluids injected into the formation to increase production of hydrocarbons.

SUMMARY

In one aspect, this disclosure generally relates to methods, systems, and devices for characterizing an anomalous fluid body in an earth formation using measurements in a borehole intersecting the formation.

General method embodiments may include galvanically exciting a transient electric field in the earth formation which interacts with an anomalous fluid body in the earth formation remote from the borehole; galvanically receiving a corresponding transient electromagnetic (TEM) signal; and using at least one processor to estimate a value of a parameter of the anomalous fluid body using the corresponding transient signal. Methods may include exciting the transient electric field at a first borehole depth and receiving the corresponding TEM signal at a second borehole depth substantially removed from the first borehole depth.

Particular embodiments may include using an elongate conductor to perform galvanically exciting the electric field and/or using a galvanic receiver to perform galvanically receiving the corresponding TEM signal. The elongate conductor may comprise installed casing, and the galvanic receiver may be below the casing in the borehole.

The transient electric field may generate time-dependent induced charges at an interface between the anomalous fluid body and the surrounding volume of the formation, and the corresponding transient electromagnetic (TEM) signal may result from the time-dependent induced charges.

Methods may include estimating a change in the parameter over time; estimating fluid movement using the estimated change in the parameter; creating a model of the formation using the estimated value of the parameter; and conducting secondary recovery operations in dependence upon the model. The parameter may be at least one of: i) a distance from the tool to the interface; and ii) at least one dimension of the fluid body. The anomalous fluid body may be a water-flooded zone resulting from injection of water to the earth formation through an injector well borehole intersecting the earth formation.

System embodiments may include a transmitter configured to, when positioned in a borehole, galvanically excite a transient electric field in the earth formation which interacts with an anomalous fluid body in the earth formation remote from the borehole; a receiver configured to, when positioned in the borehole below the transmitter, galvanically receive a corresponding transient electromagnetic (TEM) signal; and at least one processor configured to estimate a value of a parameter of the anomalous fluid body using the corresponding TEM signal. The at least one processor may include one or more computer processors operatively coupled with at least one computer memory and configured so the computer memory is accessible to the at least one processor. The computer memory may be implemented as a non-transitory computer readable medium having disposed thereon computer program instructions for implementing the methods described herein.

Examples of certain features of the disclosure have been summarized rather broadly in order that the detailed description thereof that follows may be better understood and in order that the contributions they represent to the art may be appreciated. Additional features of the disclosure will be described hereinafter.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIGS. 6A & 6B illustrate an earth model and field anomaly $F_{anomaly}(t)$ distribution with respect to depth and time responsive to an anomalous body implemented as a waterflood area in accordance with embodiments of the present disclosure;

DETAILED DESCRIPTION

Figure 1:
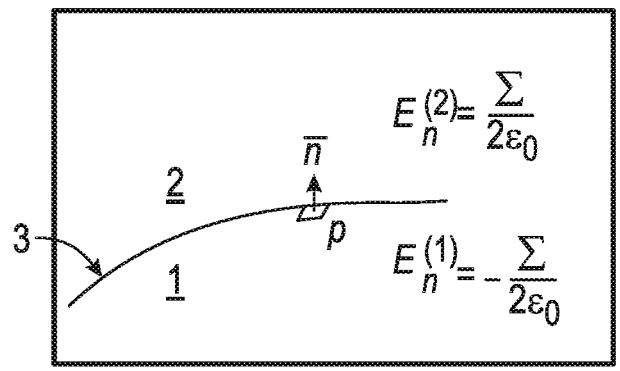
FIG. 1 illustrates electrical phenomena at a media interface in accordance with embodiments of the present disclosure.

Aspects of the present disclosure relate to systems, apparatuses and methods for galvanic electromagnetic well logging for evaluating an earth formation. Some aspects relate particularly to estimating characteristics of the formation relating to transient electromagnetic (TEM) measurements. The formation may be intersected by a wellbore.

Electromagnetic induction resistivity instruments have been used for some time to determine the electrical conductivity of earth formations surrounding a wellbore. These wireline logs have traditionally been limited to depths of investigation no more than a few feet from the surveyed wellbores. More recently, development of deep looking tools based on transient field behavior, which may capable of formation evaluation at distances ranging from ten to one hundred meters, has been attempted.

In conventional transient electromagnetic (TEM) methods, transient electromagnetic (TEM) tools are configured to effect changes in a transmitter to induce a time-dependent current in a formation. Voltage or current pulses that are excited in the inductive transmitter initiate the propagation of an electromagnetic signal in the earth formation. The transmitter and receiver may be at the surface or within the wellbore. Induced electric currents diffuse outwards from the proximity of the transmitter into the surrounding formation. Transient signals occur in the receiver antennas, which are induced by the eddy currents in the formation. At different times, information arrives at the measurement sensor predominantly from different investigation depths. Generally, early-time signals predominantly relate to near-zone responses (lesser depths of investigation) and late-time signals predominantly relate to remote-zone responses (greater depths of investigation), so that the predominant investigation depth increases with time.

In an example transient induction tool, while the tool is in the borehole, current in a transmitter coil may drop from its initial value to 0 at a particular moment (t=0). Subsequently, measurements are taken. The currents induced in the formation begin diffusing from the region close to the transmitter coil in all the directions surrounding the transmitter. These currents induce electromagnetic field components which can be measured by receivers (e.g., induction coils) placed along the tool at some distance from the transmitter.

To increase hydrocarbon production, a fluid (e.g., water) may be injected into a hydrocarbon bearing formation. During the injection, the water-hydrocarbon contact in the porous formation may be displaced. Because this displacement is accompanied by variations in the formation resistivity, the movement of the contact may be tracked using time-lapse surface and borehole EM measurements.

Two conventional approaches to exciting electromagnetic fields are widely used: frequency domain excitation (including direct currents), and time domain excitation. Time domain (transient) measurements have an advantage over frequency domain experiments of not having a direct signal from a transmitter when the transient response from a formation is being detected. Another benefit of the time domain signals is the ability to separate in time the response of different spatial areas of the formation.

For geological, economic, and engineering reasons, primary information about fluid distribution and quantification of hydrocarbon presence in a reservoir may be limited to measurements in a wellbore. In conventional fluid evaluation and monitoring applications, data may then be interpolated between wells to infer the fluid distribution in the inter-well volumes. However, rock heterogeneities, fractures, and flow corridors (especially in carbonates) may produce uneven fluid front movements. Therefore, inter-well data interpolation may be inadequate for proper monitoring of fluid movement.

It would be desirable, for this and other reasons, to measure the reservoir far away from the wellbore (at least 100-500 meters). Such measurements would make it possible to map the fluid distribution in large areas of the reservoir beyond a surveyed wellbore. Repeated surveys could track fluid migration during production and water injection.

The present disclosure is susceptible to embodiments of different forms. There are shown in the drawings, and herein will be described in detail, specific embodiments of the present disclosure with the understanding that the present disclosure is to be considered an exemplification of the principles of the present disclosure and is not intended to limit the present disclosure to that illustrated and described herein.

Galvanic TEM

In contradistinction with conventional induction-based TEM techniques, aspects of the present disclosure are related to galvanic excitation of transient electric fields and galvanic measurement of electromagnetic signals to evaluate an earth formation, and in particular an anomalous fluid body in an earth formation. The term "galvanic" is used herein to describe apparatus, systems, and methods employing a flow of an electric current in a circuit that connects a current source to an outgoing electrode, through the earth formation to a return electrode. The electrodes may be housed on a carrier, which may be part of a tool assembly. The current source may be housed in the carrier, the tool assembly, or at the surface.

Aspects of the present disclosure include using a current galvanically injected into the earth formation to characterize a fluid body in an earth formation. Method embodiments may include galvanically exciting a transient current in the earth formation causing phenomena which interact with the fluid body; galvanically receiving a corresponding transient electromagnetic (TEM) signal; and using at least one processor to estimate a value of a parameter of the fluid body using the corresponding transient signal. A transmitter and receiver for performing methods according to the disclosure may be carried on one or more downhole tools or be permanently installed in a borehole intersecting the formation.

In general method embodiments, a transient electric field resulting from the excitation may generate induced surface charges at an interface between the anomalous fluid body and the surrounding volume of the formation, and the corresponding transient electromagnetic (TEM) signal may result from these surface charges.

Transient signals that occur in the receiving galvanic sensor ("receiver") may be responsive to an electric field generated by the induced surface charges on the surface of a saturated area. These signals contain information about formation characteristics. Thus, the receiver produces a response indicative of formation characteristics, such as, for example, a resistivity characteristic of the formation, or a distance to an interface. Electronics may be configured to measure the time-dependent transient electromagnetic (TEM) signal.

General embodiments disclosed herein relate to devices and methods for monitoring fluid movement in the earth formation over time. For example, some embodiments relate to characterizing a water-flooded zone in an earth formation using transient electrical measurements taken in a borehole intersecting the formation. These measurements may be taken periodically to detect changes over time at a specific location. A second, injector well borehole used to create the water-flooded zone. The method may include estimating dimensions of the water-flooded zone or the movement of the water-flooded zone over time.

In secondary oil recovery, an external fluid such as water, gel, or gas is injected into the reservoir through one or more injector wells in an area of the formation in fluid communication with one or more production wells. The injector wells may be sited according to a particular pattern, e.g., the five-spot pattern. Using water as an example fluid, an area having high water saturation appears in the vicinity of the injector well borehole. This area is known as a water-flooded zone. If the water propagates uniformly in all directions (which is desirable) the result may be a substantially symmetric circle-shaped cylinder with a substantially vertical longitudinal axis ('vertical cylinder'), or other target shape. If the water filtrates non-uniformly (e.g., faster in some directions than in others), this may lead to bypassed zones, early breakthrough, and a low oil recovery rate. It may be desirable to characterize the dimensions of the water-flooded zone and the distance from the borehole to the interface. It would then be possible to control the volume of water injected in dependence upon the dimensions and eventually increase the oil recovery rate.

Example embodiments include systems for monitoring fluid movement. The system may be deployed during a water injection operation. An anomalous body (e.g., a flooded area) may be created in the earth formation as a result of the injection. This body responds to a galvanic excitation of the system transmitter. The response of the body and the formation to this excitation may be a transient electromagnetic (TEM) field measured by at least one receiver. In one example, the source of the TEM field (transmitter) may be an electric line grounded in the borehole. The transmitter may be implemented as borehole casing. The electric line may be grounded to the casing. The "receiver" may be an electric line grounded in the uncased part of the borehole. This galvanic acquisition system may have a significantly improved signal level, as practically achieved in field conditions.

Surface contributions to the total anomalous signal at the receiver come from electric charges. These charges arise at interfaces between media having different resistivities—in this case, at the surface of the anomalous body—upon the interfaces being intersected by an electric field generated by the transmitter signal. Volume electric currents appearing within the body serve as a source of inductive contribution to the signal—this contribution is reflective of the volume. Both currents and charges depend on resistivity of the body and surrounding medium.

FIG. 1 illustrates electrical phenomena at a media interface in accordance with embodiments of the present disclosure. As noted above, in a conducting medium, the current field j is accompanied by the appearance of electric charges. Assuming that the conductivity σ of the medium varies continuously from place to place, and that discontinuous interfaces are absent, it is true that:

$$\text{div } j = \text{div } \sigma E = 0$$

Making use of the rules of derivation of the product of a scalar by a vector we obtain:

$$\text{div } \sigma E = \sigma \text{ div } E + E \cdot \text{grad}\sigma = 0$$

and hence $$\text{div } E = -(E \cdot \text{grad}\sigma)/\sigma$$

Finally we have the equation for density of the volume charge:

$$\delta = -\epsilon_0 (E \cdot \text{grad}\sigma)/\sigma$$

Thus a volume distribution of charge appears in a conducting medium when it is non-uniform and when the electric field is not oriented perpendicularly to the direction of maximum change in conductivity. It is clear that in areas where the medium is uniform, there are no charges and therefore the quantity div E is zero.

In an interface 3 characterized by different conductivities—that is a first medium 1 has a different conductivity than a second medium 2—surface charges can arise. Proceeding from the continuity of the normal component of current density:

$$j_n^{(1)} = j_n^{(2)}$$

or $$\sigma_1 E_n^{(1)} = \sigma_2 E_n^{(2)} \quad (1)$$

The normal component of the electric field is discontinuous at the interface. This discontinuity is caused by an electric charge with density Σ on the surface, which generates a normal component having opposite sign on either side of the surface. Equation (1) may be expressed as follows:

$$\sigma_1 \left( -\frac{\Sigma}{2\varepsilon_0} + E_n^{s-p} + E_n^0 \right) = \sigma_2 \left( \frac{\Sigma}{2\varepsilon_0} + E_n^{s-p} + E_n^0 \right) \quad (2)$$

where $\pm \dfrac{\Sigma}{2\varepsilon_0}$ is the normal component of the field caused by surface charges situated near point p; $E_n^{s-p}$ is the normal component of the field caused by the rest of the surface charges; $E_n^0$ is the normal component of the field caused by charges located outside the surface. It should be noted that components $E_n^{s-p}$ and $E_n^0$ are continuous at point p. Solving equation (2) it is obtained:

$$\Sigma = 2\varepsilon_0 \frac{\sigma_1 - \sigma_2}{\sigma_1 + \sigma_2} E_n^{av} = 2\varepsilon_0 \frac{\rho_1 - \rho_2}{\rho_1 + \rho_2} E_n^{av} = 2\varepsilon_0 k_{12} E_n^{av}$$

where $$E_n^{av} = E_n^0 + E_n^{s-p},$$

and $$k_{12} = (\rho_1 - \rho_2)/(\rho_1 + \rho_2)$$

is the contrast coefficient.

Thus, from the principle of charge conservation, the flux of the current density through any closed surface is equal to zero for a time-invariant field. Therefore, for any closed surface there will be points where the normal component of j is directed outward or inward. If the body has a resistivity ($\rho_1$) different from that the surrounding medium ($\rho_2$), the density of the surface charge is directly proportional to the contrast coefficient.

$$k_{12}=(\rho_1-\rho_2)/(\rho_1+\rho_2).$$

Aspects of the present disclosure utilize several beneficial properties of the electric field caused by the induced charges to monitor fluid movement. First, these induced charges appear on the boundary of the body being tracked, and represent an interface between the body and the remainder of the formation. If this boundary separates conductive media with resistivities $\rho_1$ and $\rho_2$, then the electric field caused by the charges depends on the contrast coefficient.

By avoiding separate measurement of the individual resistivities, distance of the boundary may be more accurately determined. A magnetic field in the medium is inversely proportional to the resistivity of the medium because the current is its source. Since the absolute value of $k_{12}$ is less than one, the electric field shows lower sensitivity to resistivity than does the magnetic field. This effect is beneficial since the goal of the monitoring is to estimate the distance to the approaching contact rather than evaluate resistivity of the body and surrounding medium.

Aspects of the present disclosure include methods for estimating the dimensions of the anomalous body (e.g., water-flooded zone) using the signals. In one example a reference value, $U_{normal}$, is obtained. For example, the voltage may be measured in the receivers prior to fluid injection. Signals in the receiver at a particular time may be compared with $U_{normal}$ to estimate the distance of the interface, such as, for example, sometime during the injection operation.

Estimation may be carried out by comparing the measured values with simulated values for bodies of various dimensions. Reservoir properties (known or estimated) and transmitter/receiver configuration may be used to simulate the magnitude of the received signals corresponding to different waterflood front positions. The measured signal may be compared with various simulated values to find the closest fit. In some embodiments, the magnitude of the signals at the receivers before injection may also be simulated and compared with $U_{normal}$ for calibration. Example of these calculations is given below.

Figure 2A:
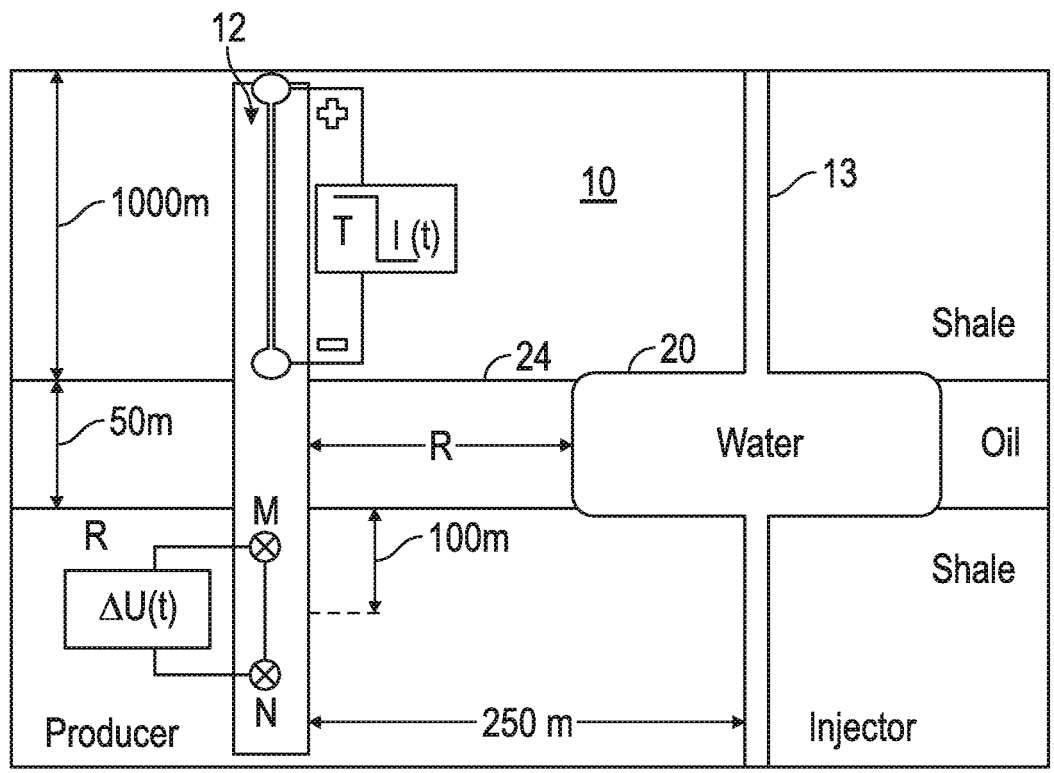
FIGS. 2A & 2B illustrate system in accordance with embodiments of the present disclosure.
Figure 2B:
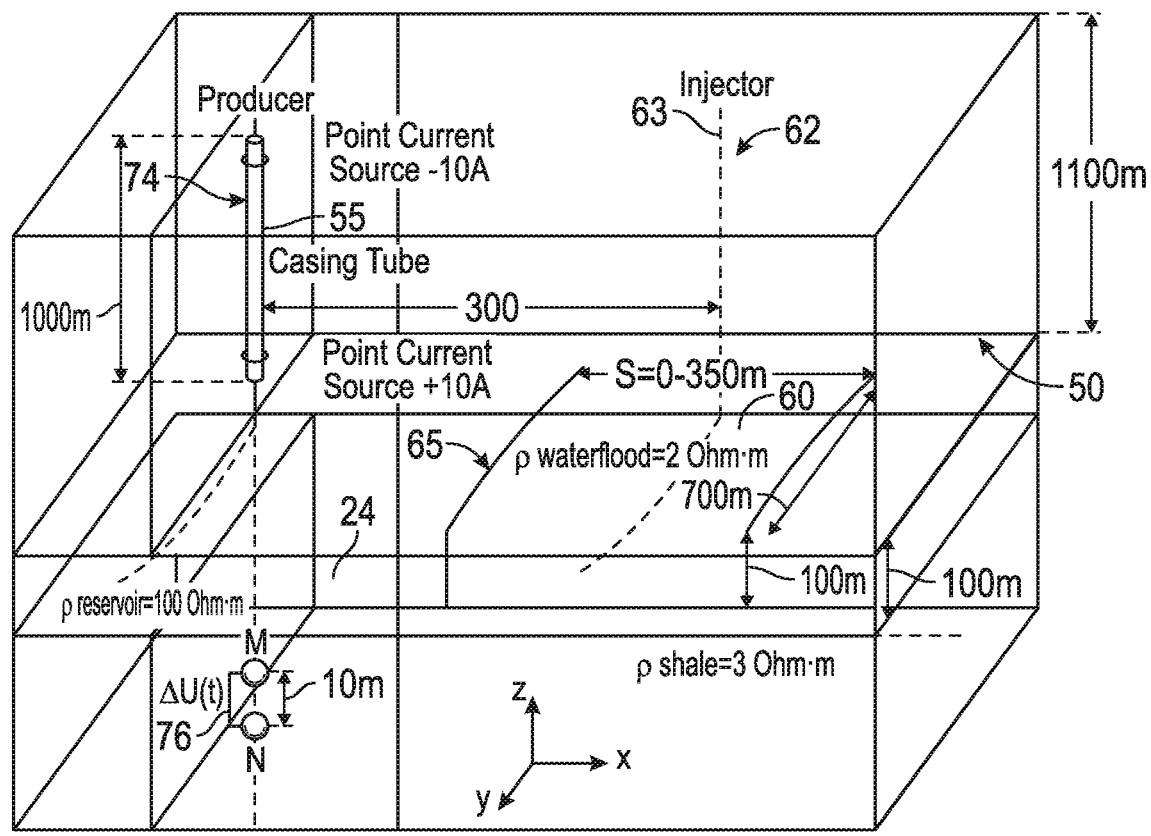

Looking forward to FIG. 2B, to estimate the signal sensitivity to the waterflood front, the voltage at the receiver line MN without a waterflood area (before the fluid injection) may be estimated. This may be referred to as the normal signal $\Delta U_{normal(t)}$. The voltage at the receiver line MN (the total signal $\Delta U_{total}$ (t)) may be simulated for the presence of a waterflood area having various widths. The voltage difference between $\Delta U_{normal\ (t)}$ and $\Delta U_{total}$ (t) is indicative of the total signal changing due to the presence of the water flood area. To estimate the total voltage sensitivity to the water fluid front moving, a series of estimations were conducted with different values of the water flood area width (S) (e.g., 150, 200, 250, 300, 350, 400, 450 and 500 meters) corresponding to respective values for range of the distance (R) between waterflood front and production well (e.g., 275, 250, 225, 200, 175, 150, 125 and 100 meters, respectively).

For given parameters of FIG. 2 B, Table 1 contains the $\Delta U_{total}$ (t) at MN receiver line (depth 1150 m) in dependence on the distance R to the water flood front and observation time t. Data presented in Table 1 demonstrate a magnitude of the total signal range that is sufficient to be measured in field conditions. This table illustrates that the closer the water flood front to the production well, the higher the total voltage difference. So the sensitivity of voltage difference to the water front movement (at the measurement point depth 1150 m) increases from 0.28 to 3.4 $\rho$V/m at the time 1•10–4 s with decreasing of R (from 275 to 100 m). The total voltage difference sensitivity to the water front movement (at the measurement point depth 1150 m) increases from 0.44 to 1.24 $\mu$V/m at the time 2•10–3 s with decreasing of R (from 275 to 100 m).

TABLE 1

The total voltage in receiver line MN. The measurement point placed in the middle of the reservoir (depth 1150 m).

| R (m) | $\Delta U_{total}$ (t), $\mu$V, t = 1 · 10$^{-4}$ s | $\Delta U_{total}$ (t), $\mu$V, t = 1 · 10$^{-3}$ s | $\Delta U_{total}$ (t), $\mu$V, t = 2 · 10$^{-3}$ s |
|---|---|---|---|
| 275 | 7228 | 4036 | 2549 |
| 250 | 7221 | 4028 | 2538 |
| 225 | 7212 | 4015 | 2523 |
| 200 | 7197 | 3996 | 2503 |
| 175 | 7175 | 3968 | 2479 |
| 150 | 7142 | 3929 | 2450 |
| 125 | 7091 | 3875 | 2419 |
| 100 | 7006 | 3805 | 2391 |

Other aspects of the present disclosure include methods for determination of the dimensions of the water-flooded zone through time-lapse measurements. The dependency of the measured signal on waterflood front movement may be estimated. Using this dependency, the boundary of the anomalous body may be tracked.

Galvanic receivers may be used to take measurements during the injection operation. The measurements may be used to detect changes in signal magnitude over time. The differences in these measurements may then be used to estimate changes in the dimensions of the anomalous body. Affects of the dimensions of the water-flooded zone on the signals may be modeled. One specific application uses such a model in conjunction with the measurement changes to reconstruct the water-flooded zone or its characteristics.

FIG. 2A shows a system in accordance with embodiments of the present disclosure. A cross-section of an earth formation 10 in which is drilled a borehole 12 is schematically represented. An anomalous body 20 of injected fluid 22 has been created in the formation 10 via fluid injection through an injector borehole 13 as part of secondary hydrocarbon recovery operations. In this instance the injected fluid is water. An interface (e.g., fluid front) exists at the boundary between the formation fluid 24 (e.g., hydrocarbons) and the body 20.

A galvanic transmitter 14 ("transmitter," T) and a receiving galvanic sensor 16 ("receiver," R) are positioned in the borehole 12. The transmitter 14 may comprise a grounded elongate conductor configured for generation of a voltage differential over its length, such as, for example, by using a plurality of electrodes spaced over the conductor (e.g., one electrode at each end of the conductor). The conductor (e.g., conductive cabling) may have a length of 200 meters or more. In some embodiments, the conductor may have a length of more than 500 meters. The receiver 16 comprises a grounded elongate conductor configured to measure a voltage differential ($\Delta U(t)$) over its length, such as, for example, by using a plurality of electrodes (M, N) spaced over the conductor (e.g., one electrode at each end of the conductor). The receiver may have a length of 5-100 meters or more. In one example, the transmitter conductor may have a length of at least 1000 meters, and the receiver conductor may have a length between 10-50 meters, inclusive.

At least one processor may be configured to control associated measurement electronics operatively electrically coupled to the transmitter and receiver to take measurements. Measurement electronics associated with the transmitter may be configured to apply a pulsed excitation of electric current to the transmitter. The pulse may be implemented as an applied direct current galvanic excitation (e.g., 10 Amps) for a short time (e.g., approximately 1000 milliseconds). Shortly (less than 1000 milliseconds) after the current in the transmitter 14 is switched off, measurement electronics associated with the receiver are configured to measure the voltage differential over the length of the receiver 16.

The transmitter and receiver may be incorporated into one or more carriers, such as downhole tools or casing. The transmitter and receiver may be individually moveable in the borehole, moveable in tandem, or permanently installed. More than one transmitter and/or receiver may be used to provide measurements corresponding to a particular borehole depth.

FIG. 2B shows another system in accordance with embodiments of the present disclosure. FIG. 2B shows a system including a galvanic transmitter 74 comprising an elongated conductor implemented as a casing tube 55 installed in a volume of an earth formation 50. An anomalous body 60 of injected fluid 62 has been created in the formation 50 via fluid injection through an injector borehole 63. An interface (e.g., fluid front) exists at the boundary between the formation fluid 24 (e.g., hydrocarbons) and the body 20. The transmitter 74 ("transmitter," T) is positioned in a borehole 52 in the formation 50, and a receiving galvanic sensor 76 ("receiver," R) is positioned below the casing in the same borehole. A respective point current source is coupled to the casing tube 55 at each end.

Referring again to FIG. 2A, a modeling approach is illustrated for estimating the effect of waterflood in a reservoir on the electric field measured in the borehole. The anomalous body 20 is modeled as an oblate spheroid. The oblate spheroid represents the anomalous body, a part of the reservoir that has been flooded via the injector. The depth of the reservoir is H=1000 m. The displaced flooded area extends from 0 to a in the r direction and from −h/2 to h/2 in the z direction (h=50 m, a=L−R). The galvanic TEM system is installed in a producing borehole (offset L=250 m). The resistivity of the shale is 200 Ohm-m; the resistivity of the oil is 20 Ohm-m; the resistivity of the water is 1 Ohm-m. An approximation method of depolarization coefficients was employed which allowed derivation of explicit estimates of a time-dependent signal measured in receiver line MN.

Table 2 illustrates the simulated values of signal $\Delta U(t)$ on the length MN of the conductor calculated for different values of the distance between water front and the producer using a measurement time $t=6 \cdot 10^{-4}$ seconds. Data presented in Table 2 demonstrates a high magnitude signal (~6 mV), which is sufficient to be measured in field conditions. A sensitivity of $\Delta U(t)$ to the water front movement is about 5.5 µV/m.

TABLE 2

Magnitude of the signal $\Delta U(t)$ calculated as a function of the distance R

| R (m) | $\Delta U(t)$, $t = 6 \cdot 10^{-4}$ s |
|---|---|
| 50 | 6300 |
| 100 | 5950 |
| 150 | 5750 |

Referring again to FIG. 2B, another modeling approach is illustrated for estimating the effect of waterflood in a reservoir on the electric field measured in the borehole. Commercially available physics modeling software suites (e.g., COMSOL MULTIPHYSICS MODELING SOFTWARE, from COMSOL, Incorporated of Burlington, Mass.) or a suitable replacement may be used to implement numerical analysis. The anomalous body 20 is represented as rectangular body with a thickness of 100 m and length of 700 m and width varying along the x-axis from 150 to 350 m. The earth model includes a mature formation (resistivity of 3 Ohm-m) with a horizontal reservoir interval (resistivity of 100 Ohm-m) having a thickness of 100 m.

Estimating the signal sensitivity to the waterflood front in the second approach may be carried out by obtaining a normal signal $\Delta U_{normal}(t)$, representing the voltage at the receiver line MN over a selected interval of the borehole without an anomalous body present (e.g., before the fluid injection); and measuring a total signal $\Delta U_{total}(t)$, reflective of the voltage at the receiver line MN in the presence of the anomalous body. The field anomaly $F_{anomaly}(t)$, caused by moving front, is defined as the relative difference between total and $$F_{anomaly}(t) = \left| \frac{\Delta U_{total}(t) - \Delta U_{normal}(t)}{\Delta U_{normal}(t)} \right| \times 100\%.$$

Figures 3A, 3B:
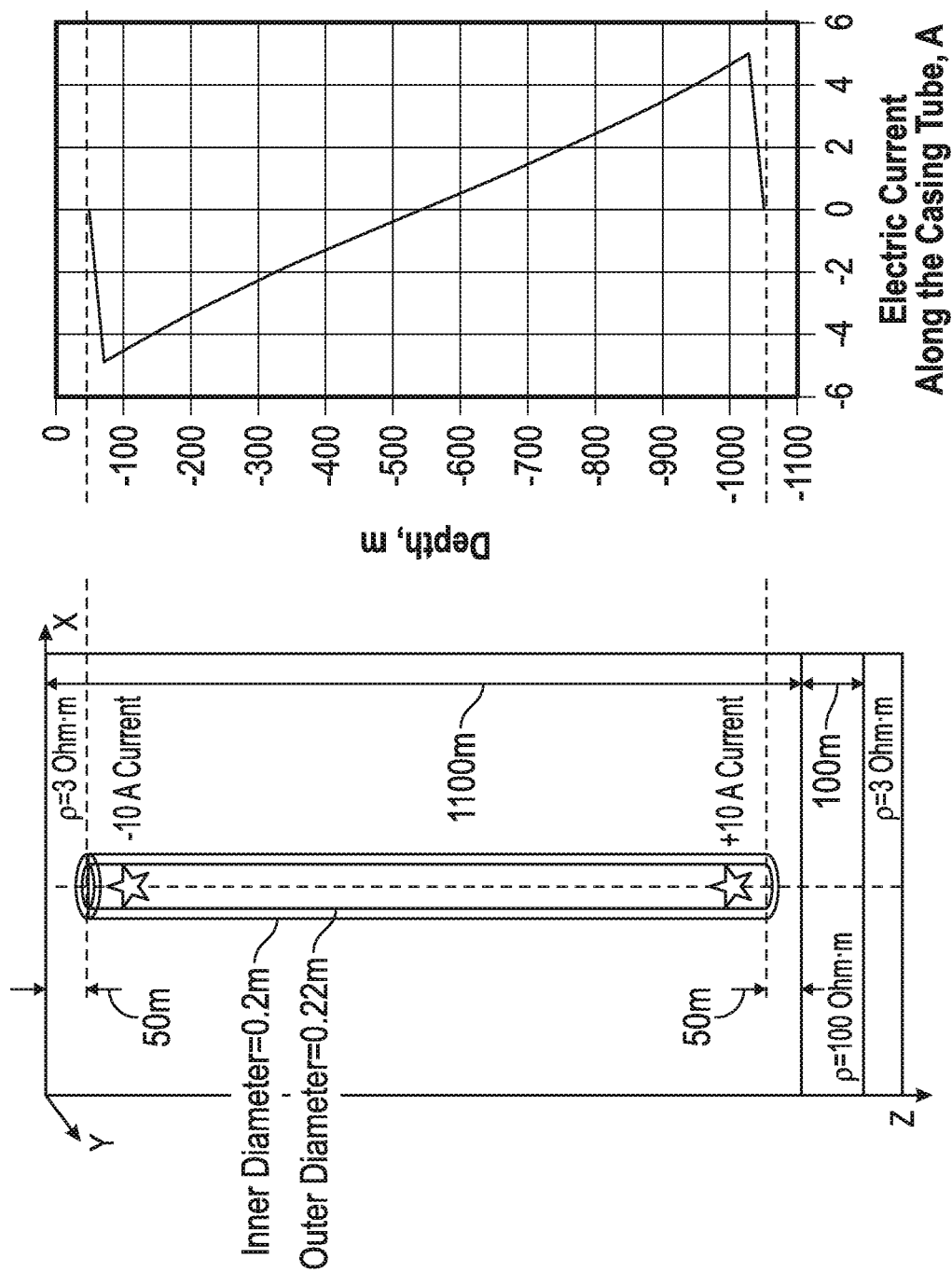
FIGS. 3A & 3B illustrate an earth model and electric current distribution due to the casing tube and the current leakage distribution along the casing tube in accordance with embodiments of the present disclosure.

FIGS. 3A & 3B illustrate an earth model and electric current distribution due to the casing tube and the current leakage distribution along the casing tube in accordance with embodiments of the present disclosure. Embodiments of the disclosure incorporate an algorithm developed to model a transient electromagnetic field along the casing tube with two grounded electrodes. The casing tube is represented as a set of electric dipoles, and then transient electromagnetic field of the entire tube is estimated via the integration of the dipole fields over the tube length. This algorithm takes into account the casing tube properties: the inner (0.2 m) and outer (0.22 m) diameter, conductivity (0.77•10**7 Sm/m), tube length, formation resistivity and placement of the grounded electrodes. The casing tube may be placed at a depth of 50 to 1050 meters. Two electrodes may be grounded to the casing tube at the depths of 70 and 1030 meters.

Estimating the signal sensitivity to the waterflood front in the second approach may be carried out by measuring the normal signal $\Delta U_{normal}(t)$ prior to the fluid injection at various borehole depths.

Figures 4A, 4B:
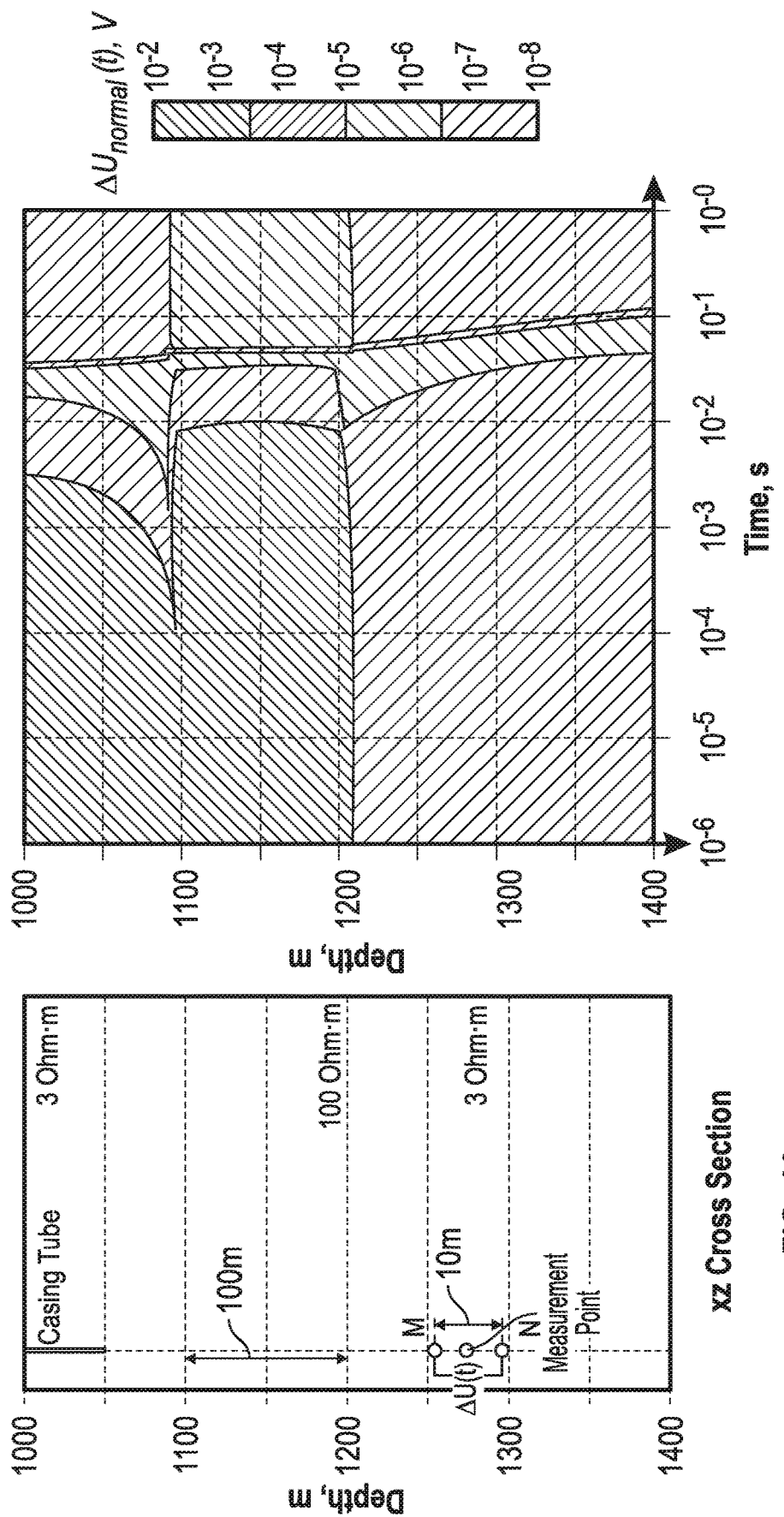
FIGS. 4A & 4B illustrate an earth model and $\Delta U_{normal}(t)$ distribution with respect to depth and time in accordance with embodiments of the present disclosure.

FIGS. 4A & 4B illustrate an earth model and $\Delta U_{normal}(t)$ distribution with respect to depth and time in accordance with embodiments of the present disclosure. Referring to FIG. 4B, the $\Delta U_{normal}(t)$ may be expressed as a color diagram presenting values of $\Delta U_{normal}(t)$ depending on the measuring time and the measurement depth. Values are shown for a measuring time between 10.6 to 1 seconds and a measurement depth ranging from 1000 to 1400 meters. It is apparent from FIG. 4B that in the middle of the reservoir a signal of 10 to 300 pV is measurable in the time range between $10^{-2}$ and $4 \cdot 10^{-2}$ seconds, when $F_{anomaly}(t)$ reaches its local maximum. $\Delta U_{normal}(t)$ below the reservoir is 1 to 10 µV in the time range of $10^{-2}$ to $5 \cdot 10^{-2}$ seconds.

Figures 5A, 5B:
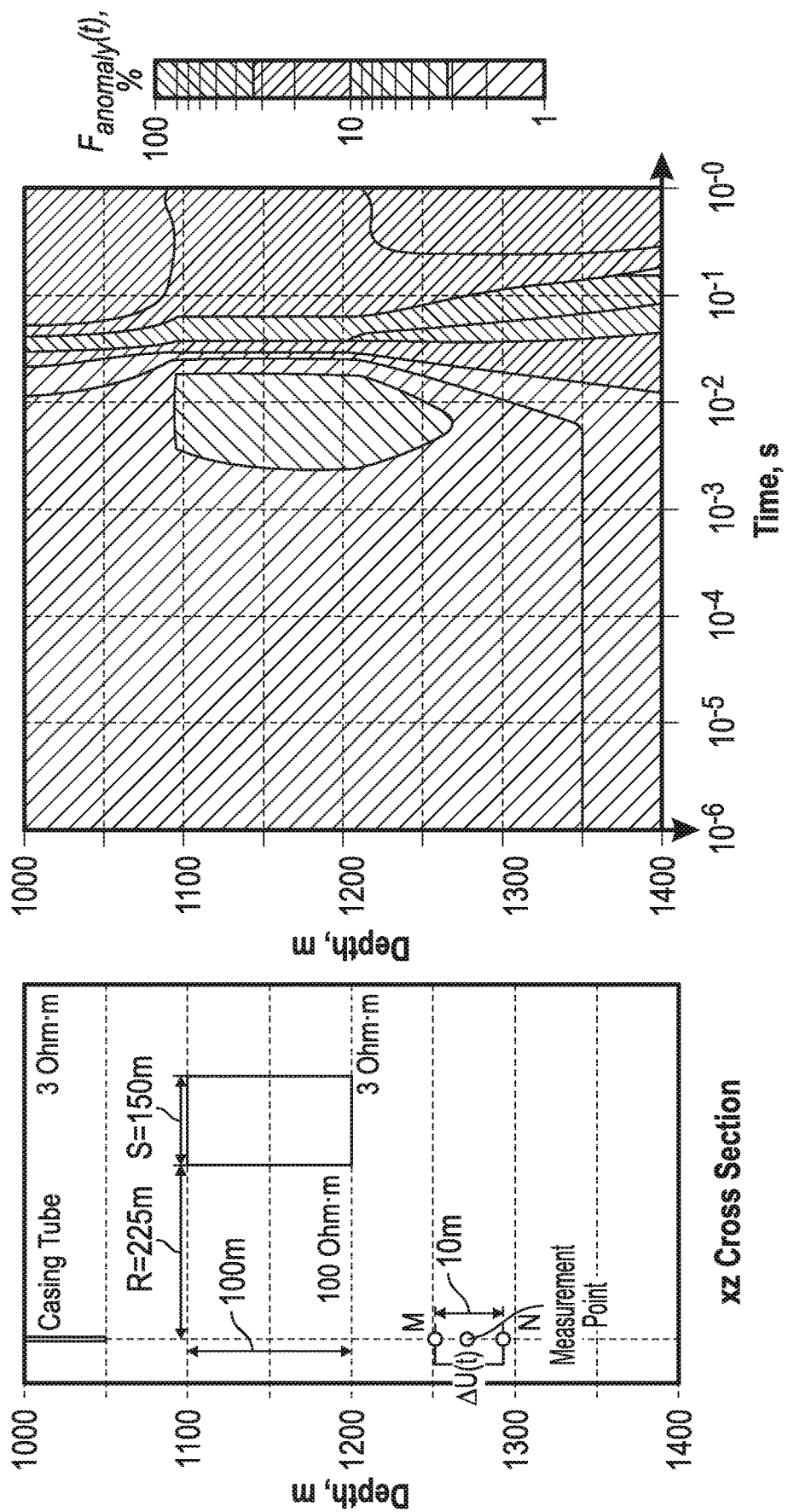
FIGS. 5A & 5B illustrate an earth model and field anomaly $F_{anomaly}(t)$ distribution with respect to depth and time responsive to an anomalous body implemented as a waterflood area in accordance with embodiments of the present disclosure.

FIGS. 5A & 5B illustrate an earth model and field anomaly $F_{anomaly}(t)$ distribution with respect to depth and time responsive to an anomalous body implemented as a waterflood area in accordance with embodiments of the present disclosure. The waterflood area has a width of 150 meters. Referring to FIG. 5B, the field anomaly $F_{anomaly}(t)$ may be expressed in percentage as a color diagram presenting values of $F_{anomaly}(t)$ depending on the measuring time and the measurement depth. Values are shown for a measuring time between $10^{-6}$ to 1 seconds and a measurement depth ranging from 1000 to 1400 meters. At a measurement depth of 1150 meters, the field anomaly $F_{anomaly}(t)$ is approximately 5 percent at approximately $10^{-2}$ seconds. $\Delta U_{normal}(t)$ has a magnitude of 200 microvolts at this measurement point. At the same depth, the field anomaly $F_{anomaly}(t)$ has a maximum (approximately 30 percent) at approximately $10^{-1}$ seconds. $\Delta U_{normal}(t)$ has a magnitude of 20 microvolts at this measurement point. Stated generally, as the measurement point increases, $F_{anomaly}(t)$ increases and $\Delta U_{normal}(t)$ decreases.

FIGS. 6A & 6B illustrate an earth model and field anomaly $F_{anomaly}(t)$ distribution with respect to depth and time responsive to an anomalous body implemented as a waterflood area in accordance with embodiments of the present disclosure. The waterflood area has a width of 350 meters. Referring to FIG. 6B, the field anomaly $F_{anomaly}(t)$ may be expressed in percentage as a color diagram presenting values of $F_{anomaly}(t)$ depending on the measuring time and the measurement depth. Values are shown for a measuring time between $10^{-6}$ to 1 seconds and a measurement depth ranging from 1000 to 1400 meters. Table 3 illustrates the approximate field anomaly $F_{anomaly}(t)$ percentage at a measurement depth of 1150 meters for different distances to the waterflood front at different approximate observation times.

TABLE 3

Measurement point in the middle of the reservoir (depth 1150 m)

| R (distance to the waterflood front, m) | $\Delta U_{normal}(t)$ (μV) | $F_{anomaly}(t)$ (%) | Observation time (s) |
|---|---|---|---|
| 225 | 200 | 5 | $10^{-2}$ |
| 125 | 200 | 8 | $10^{-2}$ |
| 225 | 20 | 30 | $10^{-1}$ |
| 125 | 20 | 80 | $10^{-1}$ |

Figure 7:
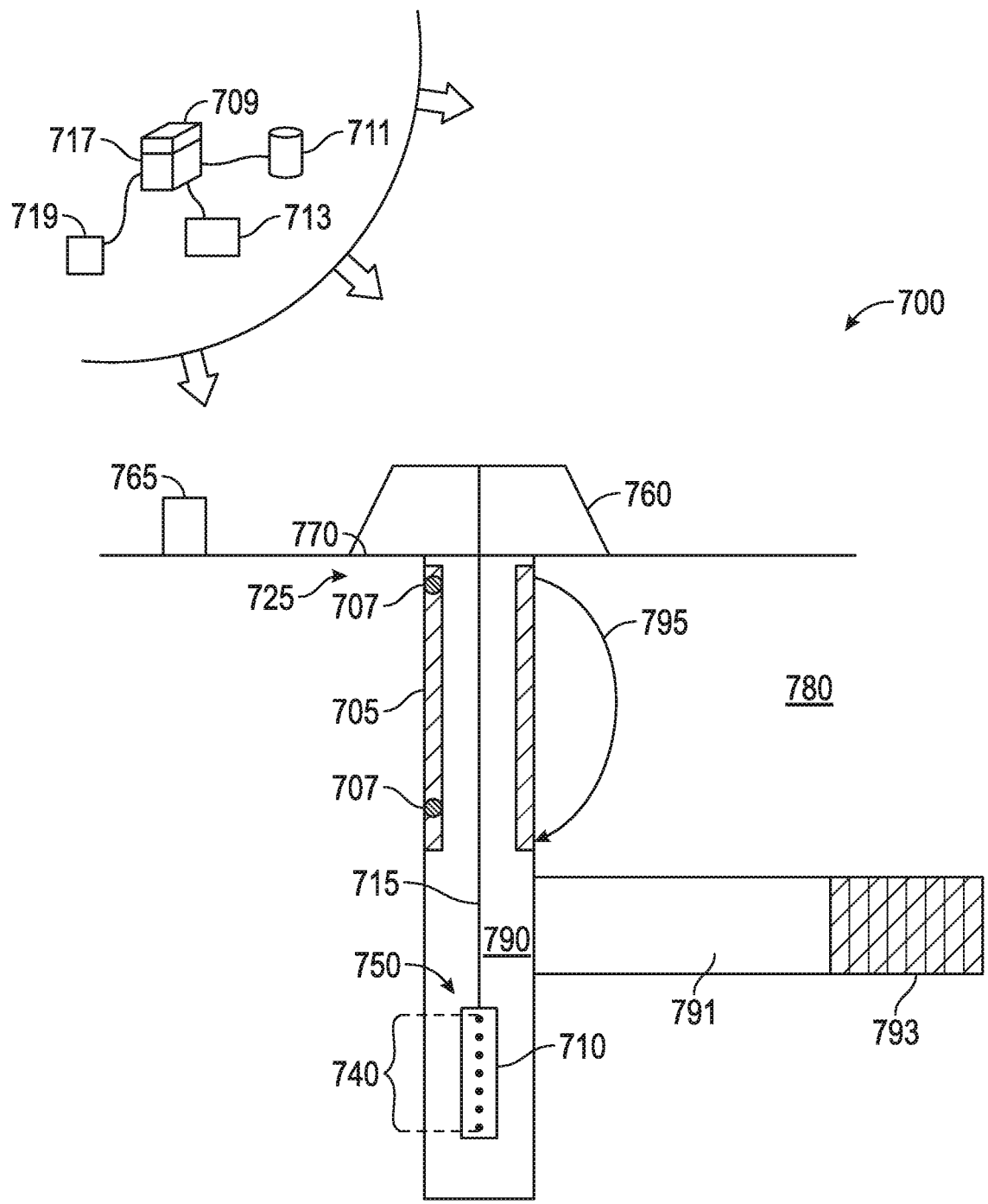
FIG. 7 schematically illustrates a resistivity imaging system in accordance with embodiments of the present disclosure.

FIG. 7 schematically illustrates a resistivity imaging system 700 having a downhole tool 710 configured to acquire information for characterizing an earth formation 780 having a horizontal reservoir interval 791 and an anomalous fluid body 793. The system 700 may include a conventional derrick 760 erected on a derrick floor 770. A conveyance device (carrier 715) which may be rigid or non-rigid, may be configured to convey the downhole tool 710 into wellbore 750 in proximity to formation 780. The carrier 715 may be a drill string, coiled tubing, a slickline, an e-line, a wireline, etc. The downhole tool 710 may include galvanic sensors 740, or in other implementation, the sensors may be installed in the wall of borehole 750 below the casing 705.

Downhole tool 710 may be coupled or combined with additional tools e.g., some or all the information processing system (inset). Thus, depending on the configuration, the tool 710 may be used during drilling and/or after the wellbore 750 has been formed. While a land system is shown, the teachings of the present disclosure may also be utilized in offshore or subsea applications.

The carrier 715 may include embedded conductors for power and/or data for providing signal and/or power communication between the surface and downhole equipment (e.g., a seven conductor cable). The carrier 715 may include a bottom hole assembly (BHA), which may include a drilling motor for rotating a drill bit. Borehole fluid (e.g., downhole fluid, or drilling fluid) 790 may be present between the formation 780 and the downhole tool 710. System 700 also includes a transmitter apparatus 725 comprising casing 705 comprising embedded electrodes 707 which serve as point current sources.

A control unit (or controller) 765 initiates galvanic excitement of a transient current 795 by generating a direct current (DC) pulse via coupling a power source to electrodes 707, and receives information regarding signals from downhole galvanic sensors 740 (and other sensors used in the system 700); the controller 765 processes such signal information according to programmed instructions provided to the control unit 765. The control unit 765 may display desired parameters and other information on a display/monitor that is utilized by an operator. The control unit 765 is shown at the surface, but may be implemented at (or may further communicate with further control units at) suitable locations on downhole tool 710 or elsewhere. The control unit 765 may process data relating to the operations and data from the sensors 740, and may control one or more downhole operations performed by system 700. The control unit 765 may be a computer-based unit that may be implemented as a hardware environment, as discussed below.

A point of novelty of the system illustrated in FIG. 1 is that the control unit 765 is configured to perform certain methods (discussed below) that are not in the prior art. A surface control unit or downhole control unit may be configured to control sensors described above and to estimate a parameter of interest according to methods described herein. Control of these components may be carried out using one or more models using methods described below.

Figure 8:
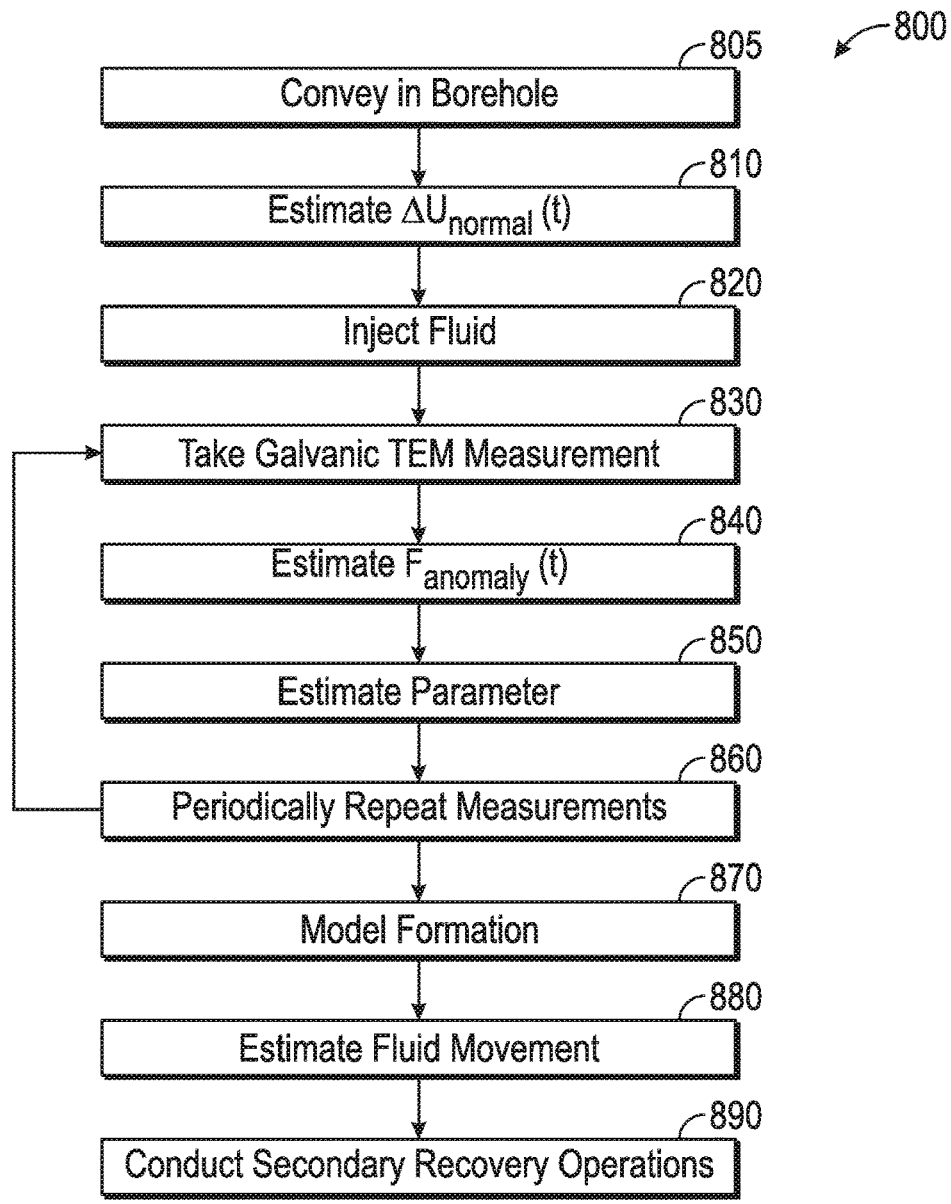
FIG. 8 shows a flow chart of one embodiment of a method for characterizing an anomalous fluid body in accordance with embodiments of the present disclosure.

FIG. 8 shows a flow chart of one embodiment of a method 800 for characterizing an anomalous fluid body (e.g., waterflooded zone) in an earth formation. Optional step 805 of the method 800 may include conveying a galvanic TEM apparatus in the borehole on at least one carrier. For example, a casing may be conveyed and installed in the borehole. The casing may be incorporated into transmitter 14, as described above. Prior to this installation, at the same time, or after the installation, a receiver (e.g., an elongate conductor) may be conveyed and installed in the borehole. Alternatively, a tool (e.g., tool 710) comprising a receiver may be conveyed on a wireline or other carrier through the casing to an area below the casing.

Method 800 includes step 810, conducting galvanic TEM measurements to estimate $\Delta U_{normal}(t)$ at a specific location at multiple depths in a borehole 12. The multiple depths may range from 0 to 1500 meters above the reservoir top. Position information may also be recorded.

In optional step 820, a fluid is injected via the injector borehole. Next is step 830, where galvanic TEM measurements are taken at a specific location at multiple depths in a borehole 12 to estimate $\Delta U_{total}(t)$. Step 840 includes estimating $F_{anomaly}(t)$ using $\Delta U_{normal}(t)$ and $\Delta U_{total}(t)$.

Step 850 includes using $F_{anomaly}(t)$ to estimate a parameter of interest of the anomalous fluid body. As one example, the distance to the interface between the fluid body and the surrounding formation may be estimated using $F_{anomaly}(t)$. Step 850 may be carried out by predicting $F_{anomaly}(t)$ for one or more values of t for each of a plurality of model water-flooded zones (e.g., for various distances to the interface) and fitting the estimated $F_{anomaly}(t)$ to one of the predicted models. In optional step 860, galvanic TEM measurements are periodically repeated.

Optional step 870 may include creating a model of the formation in dependence upon the estimated parameter. For example, the model may use estimated dimensions derived from the estimated distance to the interface. Optional step 880 may include may include estimating movement of a water-flooded zone by monitoring changes in distance from the tool to the boundary. Optional step 890 may include conducting secondary recovery operations in dependence upon the estimated parameter, the model, the estimated dimensions of the fluid body, location of the fluid body, or combinations of these. Secondary recovery operations may include any or all of drilling operations, injection operations, production operations, and the like. For example, the method may include commencing, modifying, continuing, or halting one or more injection operations in dependence upon a model of the formation including a characterization of the water-flooded zone based on the dimensions and location of the water-flooded zone.

Mathematical models, look-up tables, neural networks, or other models representing relationships between the signals and the values of the formation properties may be used to characterize operations in the formation or the formation itself, optimize one or more operational parameters of a production or development, and so on. The system may carry out these actions through notifications, advice, and/or intelligent control.

In some embodiments, multiple measurements may be taken at each depth in the borehole 12 before and/or after injection and/or at other boreholes at other locations in the formation in order to estimate dimensions of the fluid body statistically (e.g., by averaging results), for calibration, or to allow additional calculations adapted to compensate for instrument (sensor) drift, as known in the art. In other optional steps, the information may be transmitted to a processor configured to characterize the water-flooded zone.

In some embodiments, one or more of the steps may be optional. In some embodiments, some or all of the steps may be repeated, or a sequence of steps may be repeated, for example, to improve sample size without repeating all steps. At least one processor may be used to perform at least some of steps 810-890.

Figure 9:
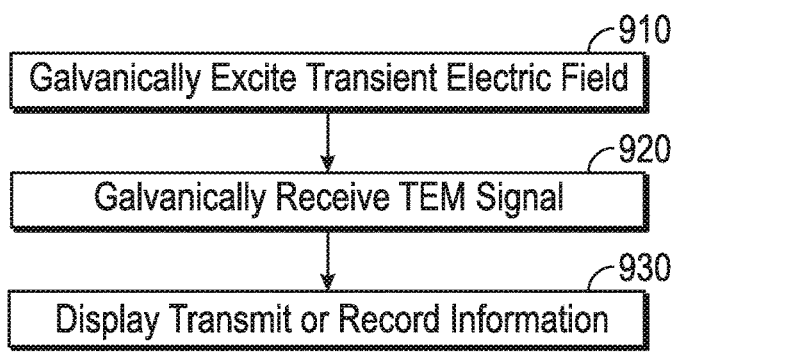
FIG. 9 illustrates a method for making a transient measurement in accordance with embodiments of the present disclosure.

FIG. 9 illustrates a method for making a transient measurement in accordance with embodiments of the present disclosure. Step 910 of the method 900 includes galvanically exciting a transient electric field in the earth formation which interacts with an anomalous fluid body in the earth formation remote from the borehole. Step 920 of the method 900 includes galvanically receiving a corresponding transient electromagnetic (TEM) signal. The signal may be generated in the receiver (or indicative of the signal generated in the receiver) and caused by the formation responsive to the current. Step 930 includes displaying, transmitting, or recording information embodying the signal.

Returning to FIG. 7, certain embodiments of the present disclosure may be implemented with a hardware environment 701 that includes an information processor 709, an information storage medium 711, an input device 713, processor memory 717, and may include peripheral information storage medium 719. The hardware environment may be at the surface, in the wellbore, in the tool 710, at the rig, or at a remote location. Moreover, the several components of the hardware environment may be distributed among those locations. The input device 713 may be any information reader or user input device, such as data card reader, keyboard, USB port, etc. The information storage medium 711 stores information provided by sensors on tool 710. Information storage medium 711 may be any non-transitory computer information storage device, such as a ROM, USB drive, memory stick, hard disk, removable RAM, EPROMs, EAROMs. EEPROM, flash memories, and optical disks or other commonly used memory storage system known to one of ordinary skill in the art including Internet based storage. Information storage medium 711 stores a program that when executed causes information processor 709 to execute the disclosed method. Information storage medium 711 may also store formation information, or the formation information may be stored in a peripheral information storage medium 711, which may be any standard computer information storage device, such as a USB drive, memory stick, hard disk, removable RAM, network based storage or other commonly used memory storage system known to one of ordinary skill in the art including Internet based storage.

Hardware environment may be any form of computer or mathematical processing hardware, including Internet based hardware. When the program is loaded from information storage medium 711 into processor memory 717 (e.g. computer RAM), the program, when executed, causes information processing device 711 to retrieve signal information from galvanic TEM measurements from either information storage medium 711 or peripheral information storage medium 719 and process the information to estimate a parameter of interest.

As used above, an information processing device is any device that transmits, receives, manipulates, converts, calculates, modulates, transposes, carries, stores, or otherwise utilizes information. In several non-limiting aspects of the disclosure, an information processing device includes a computer that executes programmed instructions for performing various methods. Herein, the term "information" may include one or more of: raw data, processed data, and signals.

The term "carrier" as used above means any device, device component, combination of devices, media and/or member that may be used to convey, house, support, or otherwise facilitate the use of another device, device component, combination of devices, media and/or member. Exemplary non-limiting carriers include drill strings of the coiled tube type, of the jointed pipe type, and any combination or portion thereof. Other carrier examples include casing pipes, wirelines, wireline sondes, slickline sondes, drop shots, downhole subs, bottom hole assemblies, drill string inserts, modules, internal housings, and substrate portions thereof.

The tool 710 may also include sensors, tools, or instruments configured to: (i) actively or passively collect information about the various characteristics of the formation, (ii) provide information about tool orientation and direction of movement, (iii) provide information about the characteristics of the reservoir fluid and/or (iv) evaluate reservoir conditions (e.g., formation pressure, wellbore pressure, temperature, etc.). Exemplary devices may include resistivity sensors (for determining the formation resistivity, dielectric constant and the presence or absence of hydrocarbons), acoustic sensors (for determining the acoustic porosity of the formation and the bed boundary in the formation), nuclear sensors (for determining the formation density, nuclear porosity and certain rock characteristics), and nuclear magnetic resonance sensors (for determining the porosity and other petrophysical characteristics of the formation). Other exemplary devices may include gyroscopes, magnetometers, and sensors that collect formation fluid samples and determine the characteristics of the formation fluid, which include physical characteristics and chemical characteristics.

In some embodiments, the borehole 12 may be utilized to recover hydrocarbons. In other embodiments, the borehole 12 may be used for geothermal applications, water production, mining, tunnel construction, or other uses.

The term "information" as used herein includes any form of information (analog, digital, EM, printed, etc.). As used herein, a processor is any information processing device that transmits, receives, manipulates, converts, calculates, modulates, transposes, carries, stores, or otherwise utilizes information. In several non-limiting aspects of the disclosure, a processor includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

Thus, configuration of the processor may include operative connection with resident memory and peripherals for executing programmed instructions. In some embodiments, estimation of the parameter of interest may involve applying a model. The model may include, but is not limited to, (i) a mathematical equation, (ii) an algorithm, (iii) a database of associated parameters, or a combination thereof.

As used herein, the term "anomalous fluid body" refers to a substantially coherent fluid body of significant size having a value of a property that is outside a normal range for a body of otherwise similar (uncorrelated) characteristics for the earth formation. The anomalous nature of the body (and property) may relate to a change in a value of a property from a normal value that exists prior to injection to another value resulting from injection.

As used herein, the term "fluid" and "fluids" refers to one or more gasses, one or more liquids, and mixtures thereof. "Hydrocarbon fluid" refers to a fluid containing at least one hydrocarbon. Well fluid refers to fluids relating to a well intersecting a subterranean earth formation. Well fluid from a subterranean formation may refer to either a fluid in a formation or a borehole intersecting a formation; a fluid recovered from a formation or a borehole intersecting a formation; fluids introduced to well; or otherwise related to the well, e.g., as part of exploration, development, completion, or production. A "downhole fluid" as used herein includes any gas, liquid, flowable solid and other materials having a fluid property, and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof. Well fluids may include, any of hydrocarbon fluids, downhole fluids, stimulation fluids, fracking fluids, additives for oil field fluids, mud filtrates, completion fluids, cement slurries, and so on.

Fluid contact, as used herein, refers to an interface that separates fluids of different electrical properties in a reservoir. The term "interface" includes a fluid interface between two different fluids in an earth formation (e.g., a fluid front). Examples following use distance to fluid fronts for convenience of illustration, but it should be readily apparent that embodiments wherein distance to an interface of a different type is estimated are within the scope of the disclosure.

"Substantially removed," as used herein, refers to a distance of greater than 50 meters. The earth formation, and particular volumes thereof, may include a porous matrix of rock and any saturated fluid contained therein.

Transient signals are those signals comporting with transient field behavior, as differentiated from continuous wave (e.g., sinusoidal) electromagnetic signals. As a result of a short pulse, at different times, information arrives at the measurement sensor from different investigation depths. The term transient should not be confused with time-lapse measurements.

The term "predominantly" relates to a property or effect (e.g., an amount of current induced) stemming from a particular source (e.g., at a depth of investigation in the earth formation, resulting from a particular physical phenomena, etc.) relative to that from another source. For example, a predominantly greater amount of current induced in the depth of interest will provide a response of electromagnetic energy that can be related to a property of the earth formation at the depth of investigation. As used herein with relation to depth of investigation, the term "predominantly" relates at least to a minimum amount of increase in currents induced at the depth of investigation with respect to other depths, the minimum amount being necessary to be able to estimate a property of the earth formation at the depth of investigation from the response. As used herein with relation to physical phenomena creating signal effects, the term "predominantly" relates at least to a minimum amount of increase in voltage measured from the physical phenomenon with respect to other phenomena, the minimum amount being necessary to be able to estimate a property of the earth formation from the response attributable to the phenomena.

Remote from the borehole, as used herein, is used to define a distance from the borehole farther than can be measured by conventional induction-based transient systems with sufficient reliability and resolution to conduct inter-well reservoir monitoring, and may include distances of at least 50 meters from the borehole wall, at least 100 meters from the borehole wall, at least 200 meters from the borehole wall, at least 400 meters from the borehole wall, and so on.

The phrase "a second borehole depth substantially removed from a first borehole depth," as used herein, refers to a distance between the borehole depths over which conventional resistivity measurements are not reliably operable, and may include distances of at least 20 meters, at least 50 meters, at least 100 meters, at least 150 meters, and so on Elongate conductor, as used herein, refers to a conductor having a length at least 20 times its width. Referring to an object as "below the casing," as used herein, refers to complete separation (e.g., a lack of overlap) between the object and the casing along the longitudinal axis of the borehole.

While the disclosure has been described with reference to exemplary embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A method of characterizing an anomalous fluid body in an earth formation using measurements in a borehole intersecting the formation, the method comprising:
    galvanically exciting a transient electric field in the earth formation which interacts with the anomalous fluid body in the earth formation remote from the borehole;
    galvanically receiving a corresponding transient electromagnetic (TEM) signal; and
    using at least one processor to estimate a value of a parameter of the anomalous fluid body using the corresponding TEM signal.

2. The method of claim 1, comprising using an elongate conductor to perform galvanically exciting the electric field.

3. The method of claim 2, comprising using a galvanic receiver to perform galvanically receiving the corresponding TEM signal, wherein the elongate conductor comprises installed casing, and the galvanic receiver is below the casing in the borehole.

4. The method of claim 1, wherein the transient electric field generates time-dependent induced charges at an interface between the anomalous fluid body and the surrounding volume of the formation, and the corresponding TEM signal results from the time-dependent induced charges.

5. The method of claim 1, comprising exciting the transient electric field at a first borehole depth and receiving the corresponding TEM signal at a second borehole depth substantially removed from the first borehole depth.

6. The method of claim 1, further comprising estimating a change in the parameter over time.

7. The method of claim 6, further comprising estimating fluid movement using the estimated change in the parameter.

8. The method of claim 1, wherein the parameter comprises at least one of: i) a distance from an interface to a tool on which at least one of the transmitter and the receiver are disposed; and ii) at least one dimension of the anomalous fluid body.

9. The method of claim 1, wherein the anomalous fluid body comprises a water-flooded zone resulting from injection of water to the earth formation through an injector well borehole intersecting the earth formation.

10. The method of claim 1, further comprising creating a model of the formation using the estimated value of the parameter.

11. The method of claim 10, further comprising conducting secondary recovery operations in dependence upon the model.

12. A system for characterizing an anomalous fluid body in an earth formation using measurements in a borehole intersecting the formation, the system comprising:
    a transmitter configured to, when positioned in a borehore, galvanically excite a transient electric field in the earth formation which interacts with the anomalous fluid body in the earth formation remote from the borehole;
    a receiver configured to, when positioned in the borehole below the transmitter, galvanically receive a corresponding transient electromagnetic (TEM) signal; and
    at least one processor configured to estimate a value of a parameter of the anomalous fluid body using the corresponding TEM signal.

* * * * *